United States Patent [19]

Schmolka

[11] 4,387,217

[45] Jun. 7, 1983

[54] HIGH FOAMING IODOPHORS

[75] Inventor: Irving R. Schmolka, Grosse Ile, Mich.

[73] Assignee: BASF Wyandotte Corporation, Wyandotte, Mich.

[21] Appl. No.: 366,454

[22] Filed: Apr. 7, 1982

[51] Int. Cl.³ .................... C08L 71/02; C08G 65/32
[52] U.S. Cl. .................................. 528/417; 525/410;
 252/106; 528/405; 568/614; 568/624
[58] Field of Search ............... 525/410; 528/405, 417;
 568/614, 624

[56] References Cited

U.S. PATENT DOCUMENTS

| 3,438,906 | 4/1969 | Duvall | 568/624 X |
| 3,438,907 | 4/1969 | Schmolka | 568/624 X |
| 4,042,525 | 8/1977 | Ackermann et al. | 568/624 X |
| 4,200,733 | 4/1980 | Perner et al. | 528/417 |

Primary Examiner—Earl A. Nielsen
Attorney, Agent, or Firm—Joseph D. Michaels

[57] ABSTRACT

An iodophor containing a polyoxybutylene-polyoxyethylene nonionic block copolymer has unexpectedly high foam.

3 Claims, No Drawings

HIGH FOAMING IODOPHORS

BACKGROUND OF THE INVENTION

1. Field of the Invention

The invention relates to an iodophor containing iodine and a cogeneric mixture of conjugated polyoxybutylene-polyoxyethylene compounds. The iodophor is more dispersible, higher foaming and less viscous than similar iodophors made with polyoxyethylene-polyoxypropylene compounds and is higher foaming when compared with iodine containing block copolymers of 1,4-butylene oxide and ethylene oxide.

2. Description of the Prior Art

U.S. Pat. No. 4,200,733 relates to iodine containing block copolymers of 1,4-butylene oxide and ethylene oxide which contain from 5 to 25 percent by weight of bonded iodine, and are based on iodine free compounds containing 1,4-oxybutylene and oxyethylene units. The iodophors are disclosed as being useful in disinfectant cleansers, for example, in the beverage industry and as sanitizers in meat packing plants in dairies and other processing plants.

One of the problems of prior iodophors is low foaming. The present invention is directed to the preparation of a high foaming iodophor.

SUMMARY OF THE INVENTION

The invention relates to an iodophor comprising from 0.01 to 10.0 percent by weight of bonded iodine and a polyoxybutylene-polyoxyethylene block copolymer. The block copolymer is a cogeneric mixture of conjugated polyoxybutylene-polyoxyethylene compounds containing in their structure oxybutylene groups, oxyethylene groups and an organic radical derived from an organic compound containing a plurality of reactive hydrogen atoms, preferably a water soluble organic compound containing a plurality of reactive hydrogen atoms and 2 to 12 carbon atoms. The compounds are characterized in that all the oxybutylene groups are present in polyoxybutylene chains that are attached to the organic radical at the site of a reactive hydrogen atom, thereby principally constituting a polyoxybutylene polymer. The oxyethylene groups are attached to the polyoxybutylene polymer in polyoxyethylene chains. The average molecular weight of the polyoxybutylene polymers in the mixture is at least 500, as determined by hydroxyl number, and the oxyethylene groups present constitute 65 to 80 percent by weight of the compound.

In a preferred embodiment the average molecular weight of the polyoxybutylene polymer is between 600 and 1200. The iodophors are useful in dilute solution for a hand soap, as a shampoo, and, for sanitizing food handling equipment in food processing plants, such as dairies and meat packing plants.

The iodophors of the invention provide unexpectedly higher foaming compositions than the polyoxypropylene-polyoxyethylene compositions of the past, and in particular than the compositions containing block copolymers of 1,4 butylene oxide and ethylene oxide of the prior art.

DESCRIPTION OF THE PREFERRED EMBODIMENT

The block copolymer of use in the invention is a cogeneric mixture of conjugated polyoxybutylene polyoxyethylene compounds having as a hydrophobe, a polyoxybutylene polymer of at least 500 molecular weight. The polyoxybutylene compounds are prepared by first condensing butylene oxide with a water soluble organic compound containing a plurality of reactive hydrogen atoms to prepare a polyoxybutylene polymer of at least 500 molecular weight, and subsequently condensing ethylene oxide thereto. The compounds used in this invention conform to the following generic formula:

$$Y[(C_4H_8O)_n\text{—E—H}]_x \qquad (A)$$

wherein Y is the residue of a water soluble organic compound containing therein x active hydrogen atoms; n is an integer; x is an integer greater than 1; the values of n and x are such that the molecular weight of the compound, exclusive of E, is at least 500, as determined by hydroxyl number; E is a polyoxyalkylene chain wherein the oxygen/carbon atom ratio is at least 0.5, and E constitutes 65 percent by weight to 80 percent by weight of the compound.

The polyoxybutylene polymer, which is an intermediate in the preparation of the compounds of use in this invention, has the following structure:

$$Y[(C_4H_8O)_n H]_x \qquad (B)$$

wherein Y, n and x are defined as in Formula A above.

The preferred compounds of use in this invention are prepared by condensing ethylene oxide in an amount between 65 and 80 percent by weight of the resultant compound with the polyoxybutylene polymer. These compounds have the following formula:

$$Y[(C_4H_8O)_n(C_2H_4O)_m H]_x \qquad (C)$$

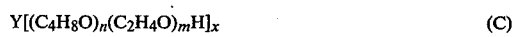

wherein Y, n and x are defined as in Formula A and m has a value such that the oxyethylene groups constitute 65 to 80 percent by weight of the compound.

When ethylene oxide is condensed with a polyoxybutylene glycol of at least 500 molecular weight and derived from a butanediol initiator, the resulting compounds have the following structure:

$$HO(C_2H_4O)_m(C_4H_8O)_n(C_2H_4O)_{m'}H \qquad (D)$$

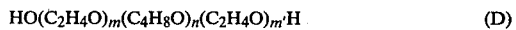

where n is defined as previously set forth; and $m'+m$ have a value such that the oxyethylene groups constitute 65 percent by weight to 80 percent by weight of the compound.

The hydrophilic portion of the polyoxyalkylene compounds may be supplied in whole or in part by other polyoxyalkylene chains in lieu of the polyoxyethylene chain set forth in Formula C. Any polyoxyalkylene chain may be used provided that the oxygen/carbon ratio contained therein is at least 0.5.

The butylene oxide used in making the hydrophobic polyoxybutylene polymer, which is an intermediate in the preparation of the compounds used in this invention, and is represented by the formula 1,2-butylene oxide, may be replaced with up to 10 percent by weight of propylene oxide or ethylene oxide when added as a mixture with butylene oxide. Also, up to 10 percent by weight of propylene oxide or 1,2-butylene oxide may be used to replace ethylene oxide, when added as a mixture with ethylene oxide, in preparing the block copolymers used in this invention.

Block copolymers of this invention, conforming to structure D above, are those block copolymers which contain a hydrophobe of between about 600 and about 1200 molecular weight and an ethylene oxide content of from about 65 to 80 percent by weight of the block copolymer. Preferably used is a block copolymer having a hydrophobe of about 1200 molecular weight and containing about 70 percent by weight ethylene oxide.

The iodophors of the invention are prepared by treating the block copolymer with an amount of elementary iodine such that the iodophor contains from 0.01 to 10.0, preferably from 0.1 to 5 percent by weight of bonded iodine. The block copolymer content in a preferred embodiment is between 0.1 to 50.0 percent by weight, more preferably 10 to 25 percent by weight of the iodophor.

Following block copolymers A and B, made from a polyoxybutylene hydrophobe prepared from condensing 1,2-butylene oxide with a 1,4-butane diol initiator, and comparison M are used in the examples: block copolymer A is polyoxybutylene-polyoxyethylene nonionic block copolymer of this invention having an approximate average molecular weight of a polyoxybutylene hydrophobe of about 600 and a polyoxyethylene hydrophile content of about 80 percent by weight of the block copolymer.

Block copolymer B is a polyoxybutylene-polyoxyethylene nonionic block copolymer of this invention having an approximate average molecular weight of polyoxybutylene hydrophobe of about 1200 and a polyoxyethylene hydrophile content of about 70 percent by weight of the block copolymer.

Comparison M is polyoxypropylene-polyoxyethylene nonionic surfactant having a molecular weight of the polyoxypropylene hydrophobe of about 2250 and a polyoxyethylene hydrophile content of about 70 percent by weight of the surfactant.

The following examples will further illustrate the various aspects of the invention. Where not otherwise specified throughout this specification and claims, temperature is in degree centigrade and parts, percentages and proportions are by weight.

EXAMPLES 1 AND 2 AND COMPARISON EXAMPLE M

Examples 1 and 2, examples of the iodophors of the invention, are prepared using the following percent by weight compositions:

|    | Percent by Weight | Description |
|----|-------------------|-------------|
| A. | 15.0 | block copolymer A |
|    | 20.0 | isopropyl alcohol |
|    | 22.5 | concentrated $H_3PO_4$ |
|    | 6.25 | concentrated $H_2SO_4$ |
|    | 2.75 | iodine |
|    | 20.00 | citric acid |
|    | 13.50 | water |
|    | 100.00 | Total |
| B. | 15.0 | block copolymer B |
|    | 20.0 | isopropyl alcohol |
|    | 22.5 | concentrated $H_3PO_4$ |
|    | 6.25 | concentrated $H_2SO_4$ |
|    | 2.75 | iodine |
|    | 23.50 | water |
|    | 10.0 | citric acid |
|    | 100.0 | Total |

Comparison M was prepared as in B above using Comparison M as the nonionic. This preparation was used as a control.

The preparations of Examples A, B and M above were made as follows. The nonionic and isopropanol are placed in a three-neck 500 ml round-bottom flask, with mechanical stirrer, reflux condenser and dropping funnel. Mix slowly until homogeneous. Slowly, over a 15 minute period, add iodine, previously pulverized in a mortar and pestle. Allow to mix several hours. Slowly add acids and water, maintaining ambient temperature in flask. Final solutions are red-brown in color.

A few drops of each product are added to 400 ml of water in a 600 ml beaker. The control sank to the bottom as a dark brown oil. Vigorous stirring was needed to get the iodophor to dissipate throughout the beaker, resulting in a pale yellow solution. When each of the iodophors of Examples A or B was added to water, as above, they dispersed rapidly, with little or no stirring and also gave a pale yellow aqueous solution.

A comparison of the foam properties of Example B and Comparison M was made. The test procedure consisted of diluting 5 grams of the iodophor to 100 grams with distilled water, placing each solution in a 1000 ml measuring cylinder and rotating the cylinder at 25 rpm for 1 minute. Foam heights were read immediately and at specific time intervals. The results are shown in Table I below.

TABLE I

| Time | Example B | Comparison M |
|------|-----------|--------------|
| Initial | 200 − 20 = 180 ml | 180 − 90 = 90 ml |
| After 1 minute | 140 − 95 = 45 ml | 110 − 100 = 10 ml |
| After 5 minutes | 125 − 98 = 27 ml | 102 − 100 = 2 ml |
| After 30 minutes | 110 − 100 = 10 ml | 100 − 100 − 0 ml |

A comparison of the viscosity is shown below in Table II.

TABLE II

| rpm | Example B | Comparison M |
|-----|-----------|--------------|
| 6 | 75 cps | 200 cps |
| 12 | 75 cps | 163 cps |
| 30 | 80 cps | 140 cps |
| 60 | 80 cps | 140 cps |

The unexpected higher foam of the iodophors of the invention when compared with the prior art iodophor is shown above.

The embodiments of the invention in which an exclusive privilege or property is claimed are defined as follows:

1. An iodophor comprising 0.01 to 10.0 percent by weight of bonded iodine, and a nonionic block copolymer being a cogeneric mixture of conjugated polyoxybutylene-polyoxyethylene compounds containing in their structure oxybutylene groups, oxyethylene groups and an organic radical derived from a water-soluble organic compound containing a plurality of reactive hydrogen atoms and 2 to 12 carbon atoms; the compounds being characterized in that all of the oxybutylene groups are present in polyoxybutylene chains that are attached to the organic radical at the site of a reactive hydrogen atom thereby constituting a polyoxybutylene polymer; the oxyethylene groups being attached to the polyoxybutylene polymer in polyoxyethylene chains; the average molecular weight of the polyoxybutylene polymers in the mixture being at least 500, as determined by hydroxyl number, and the oxyethylene groups present constituting 65 to 80 percent by weight of the mixture.

2. The iodophor of claim 1 wherein the block copolymer is used in an amount between 0.1 to 50.0 percent by weight of the iodophor.

3. The iodophor of claim 1 wherein the block copolymer is a polyoxybutylene polyoxyethylene nonionic block copolymer having an approximate average molecular weight of a polyoxybutylene hydrophobe of about 600 and a polyoxyethylene hydrophile content of about 80 percent by weight of the block copolymer.

* * * * *